United States Patent
Gillespie et al.

(10) Patent No.: US 6,531,511 B1
(45) Date of Patent: Mar. 11, 2003

(54) 2-ADAMANTANEMETHANAMINE COMPOUNDS FOR TREATING ABNORMALITIES IN GLUTAMATERGIC TRANSMISSION

(75) Inventors: Roger John Gillespie, Wokingham (GB); Nathaniel Julius Thomas Monck, Wokingham (GB); Andrew James Bird, Wokingham (GB); Simon Edward Ward, Wokingham (GB)

(73) Assignee: Vernalis Research Limited, Wokingham (GB)

( * ) Notice: Subject to any disclaimer, the term of this patent is extended or adjusted under 35 U.S.C. 154(b) by 0 days.

(21) Appl. No.: 09/890,061
(22) PCT Filed: Jan. 26, 2000
(86) PCT No.: PCT/GB00/00207
§ 371 (c)(1),
(2), (4) Date: Oct. 16, 2001
(87) PCT Pub. No.: WO00/44371
PCT Pub. Date: Aug. 3, 2000

(30) Foreign Application Priority Data

Jan. 26, 1999 (GB) .............................. 9901691

(51) Int. Cl.$^7$ .............................. A61K 31/13
(52) U.S. Cl. ............. 514/662; 514/661; 544/330; 544/332; 544/362; 546/208; 546/276.4; 546/279.1; 548/530; 548/540
(58) Field of Search ................. 514/662, 661; 544/333, 330, 362; 548/530, 540; 546/208, 276.4, 279.1

(56) References Cited

U.S. PATENT DOCUMENTS 5,286,715 A * 2/1994 Vranesic et al. ............... 514/18
6,008,240 A  12/1999 Phillips et al. ............... 514/400
6,011,155 A  1/2000 Villhauer .................... 544/333

FOREIGN PATENT DOCUMENTS

| EP | 1 085 011 | 3/2001 |
| WO | 92/17168 | 10/1992 |
| WO | 99/31051 | 6/1999 |
| WO | 99/31075 | 6/1999 |
| WO | 99/38841 | 8/1999 |
| WO | 01/12189 | 2/2001 |
| WO | 01/40231 | 6/2001 |

OTHER PUBLICATIONS

Chakrabarti et al., "Adamantanealkanamines as Potential Antidepressant and Anti–Parkinsin Agents," *Journal of Medicinal Chemistry*, vol. 17, No. 6, 1974, pp. 602–609.
Porter et al., "Regional Variations in the Pharmacology of NMDA Receptor Channel Blockers: Implications for Therapeutic Potential," *Journal of Neurochemistry*, vol. 64, No. 2, 1995, pp. 614–623, Raven Press. Ltd.
Ursini et al., "Synthesis and SAR of New 5–Phenyl–3–ureido–1,5–benzodiazepines as Cholecystokinin–B Receptor Antagonists," *Journal of Medicinal Chemistry*, vol. 43, No. 20, 2000, pp. 3596–3613, American Chemical Society.
Boulch et al., "Asymmetric Cyclopropanation Catalyzed by C$_2$–Symmetric," *Tetrahedron Letters*, pp. 1023–1026, 2000, Elsevier Science Ltd.
Tomasic et al., "Comparative Study of the Effects of Peptidoglycan Monomer and Structurally Related Adamantyltripeptides on Humoral Immune response to Ovalbumin in the Mouse," *Vaccine*, vol. 18, 2000, pp. 1236–1243, Elsevier Science Ltd.
Dutton et al., "Synthesis of Hindered Spiro–Oxindoles by Photolysis of 1–(1–Alkinyl)benzotriazoles," vol. 55, 1999, pp. 11927–11942, *Tetrahedron*, Elsevier Science Ltd.
Pleynet et al., "A General Synthesis of 1–(1–Alkenyl)benzotriazoles," *Tetrahedron*, vol. 55, 1999, pp. 11903–11926, Elsevier Science Ltd.
Lukach et al., "Reactions of 2–Iodo– and 1,2–Dihaloadamantanes with Carbanions in DMSO by the S$_{rn}$1 Mechanism," *J. Org. Chem.*, vol. 64, No. 16, 1999, 5826–5831, American Chemistry Society.
Kroemer et al., "Quantitative Analysis of the Structural Requirements for Blockade of the N–Methyl–D–Aspartate Receptor at the Phencyclidine Binding Site," *Journal of Medicinal Chemistry*, vol. 41, No. 3, 1998, pp. 393–400, American Chemical Society.
Parsons et al., "Comparison of the Potency, Kinetics and Voltage–Dependency of a Series of Uncompetitive NMDA Receptor Antagonists In Vitro with Anticonvulsive and Motor Impairment Activity In Vivo," *Neuropharmacology*, vol. 34, No. 10, 1995, pp. 1239–1258, Elsevier Science Ltd.
Fytas et al., "3–Cyclopentyl–1–Adamantanamines and Adamantanemethanamines Antiviral Activity Evaluation and Convulsions Studies," *Il Farmaco*, vol. 49, No. 10, 1994, pp. 641–647.
Madder et al., "Mechanism of Esterification of 1,3–Dimethylamino Alcohols by N–Acetylimidazole in Acetonitrile and the Influence of Alkyl and Geminal Dialkyl Substitution Upon the Rate," *J. Chem. Soc.*, 1997, pp. 2787–2793.
Abstract, Rossi et al., Electron Transfer in Nucleophilic substitution Reactions: Effect of the Leaving Group and Substituents, 4$^{th}$ *Lat. Am. Conf. Phys. Org. Chem.*, 1999, pp. 72–90, Universidade Federal de Santa Catarina.
Abstract, Tokuyama et al., "A Novel Synthesis of 2,3–Disubstituted Indoles by Radical Cyclization of 2–Alkenylthioanilides and its Applications," *Tennen Yuki Kagobutsu Toronkai Koen Yoshishu*, (41), 1999, pp. 61–66.

* cited by examiner

*Primary Examiner*—Dwayne C. Jones
(74) *Attorney, Agent, or Firm*—Foley & Lardner

(57) ABSTRACT

The use of a compound of formula (1), as disclosed in the specification, wherein R$_1$, R$_2$, R$_3$, R$_4$, R$_5$ and R$_6$ are independently selected from hydrogen, alkyl and aryl, or pharmaceutically acceptable salts thereof, with the proviso that wherein R$_1$ to R$_4$ and R$_6$ are hydrogen, R$_5$ is not selected from CH$_2$CH$_2$NHSO$_2$CH$_3$, CH$_2$CH$_2$NHSO$_2$CF$_3$ and methyl substituted by SO$_2$NH$_2$, SO$_3$H, PO$_3$H$_2$, CONHOH or a heterocyclic group selected from formulae (a), (b), (c), (d) and (e) in the manufacture of a medicament for use in the treatment of a condition generally associated with abnormalities in glutamatergic transmission.

27 Claims, No Drawings

2-ADAMANTANEMETHANAMINE COMPOUNDS FOR TREATING ABNORMALITIES IN GLUTAMATERGIC TRANSMISSION

The present application is a national stage application of PCT Application No. PCT/GB00/00207, filed Jan. 26, 2000, which claims the benefit of United Kingdom Application No. GB 990691.7, filed Jan. 26, 1999.

BACKGROUND OF THE INVENTION

The present invention relates to compounds and compositions for use in the treatment of conditions generally associated with abnormalities in glutamatergic transmission.

The excitatory neurotransmission underlying brain function is primarily (about 80 per cent) dependent on the action of glutamate and other related neurotransmitters on specific receptors activated by the excitatory amino acids. These receptors fall into several categories, one of which is the glutamate receptor specifically sensitive to the agonist N-methyl-D-aspartate (the NMDA receptor). NMDA receptor subtypes are ubiquitously expressed in mammalian brain and have unique properties underlying their role in synaptic function and plasticity. In view of the central role of these receptors in normal central nervous system function, numerous suggestions have been made as to the utility of drugs acting at this receptor to modulate the processes underlying various disease states. The NMDA receptor has been studied with particular interest in relation to its apparent involvement in the pathophysiology of neurodegenerative diseases.

Non-competitive antagonists at this receptor should be particularly advantageous in the treatment of diseases since such compounds would have activity that should not be overcome by high levels of endogenous agonists and would act equally well independent of the endogenous agonist activating the receptor. This is important since high levels of endogenous glutamate can occur in certain pathological processes and there are a variety of different endogenous agonists that can act through a variety of specific modulatory agonist binding sites on the receptor.

A number of NMDA antagonists have been disclosed which operate by binding to the ion-channel of the NMDA receptor. The advantage of channel blockers is that they operate only on the "open" channel and therefore do not affect unactivated receptors. In addition they are effective regardless of the mechanism of receptor stimulation and their effect will not be diminished by large concentrations of endogenous agonist.

Given that the NMDA receptor plays a primary role in normal central nervous system function, it is not surprising that certain drugs acting to block or antagonise the function of this receptor affect normal function within the brain. This may be manifested as central nervous system side effects such as hallucinations, confusion, paranoia, aggression, agitation and catatonia. These side effects can be described as a psychotic state and the drugs that induce them are known as psychotomimetic NMDA antagonists. Such side effects limit the utility of these compounds in treating disease states. NMDA receptor antagonists that have efficacy in treating central nervous system disorders but without such psychotomimetic side effects would have a clear therapeutic advantage. Thus, in view of the crucial role played by the NMDA receptor in either the progression or expression of the disease pathology and process, it is an object of this invention to provide compounds for the treatment of central nervous system disorders which modulate the activity of the NMDA receptor but which are well-tolerated in the sense of having a markedly reduced propensity to induce psychotomimetic side effects.

The present invention is particularly concerned with the treatment of neurodegenerative disorders. There is a large body of evidence to suggest that either an excitotoxic or slow excitotoxic pathological over-activation of the NMDA receptor induces the death of neurons in a variety of disorders such as ischaemic stroke, other forms of hypoxic injury, haemorrhagic brain injury, traumatic brain injury, Alzheimer's disease, Parkinson's disease, Huntington's disease and other dementing diseases. There is thus clear evidence that antagonism of the NMDA receptor will reduce or prevent the neurodegeneration that underlies the disease process in these and related conditions. There is also evidence to suggest that a well-tolerated compound will allow effective symptomatic treatment of the manifestations of the disease process in these disorders as well as reducing the primary underlying neurodegeneration process. Also, it is known that disorders previously described as involving acute neurodegeneration have longer than expected elevations in glutamate release and consequently require longer than expected treatment with NMDA antagonists. There would therefore be a therapeutic advantage for new drugs which are well-tolerated and which can therefore be administered chronically.

The published literature contains references to a number of compounds and classes of compounds purported to be useful as NMDA antagonists.

The compounds Amantadine and Memantine and related anti-viral agents have been known for many years.

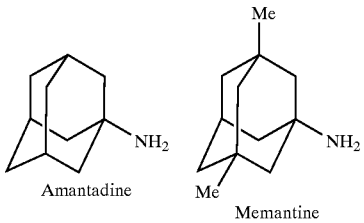

Patent applications have been filed directed to the use of Memantine in the treatment of Parkinson's Disease in the 1970s and as an NMDA antagonist in 1990 (see EP-A-0392059 and U.S. Pat. No. 5,061,703). Furthermore, International Patent application WO94/05275 proposes the use of Amantadine and related compounds such as Memantine in the treatment and prevention of non-ischaemic, long term NMDA receptor-mediated neuronal degeneration. An increase in affinity for the NMDA receptor due to substitution of the adamantane ring of Amantadine with alkyl groups was noted and published by Komhuber et al. (Eur. J. Pharmacol., 1991, 206, 297–300). Structure-activity relationships relating to 1-(adamantyl)alkanamines are reported by Kroemer et al. (J. Med. Chem.,1998, 41, 393–400), by Parsons et al. (Neuropharmacology, 1995, 34, 1239–1258) and by Fytas et al. (Il Farmaco,1994, 49, 641–647).

As discussed above, psychotomimetic side-effects are observed during the use of a number of well known NMDA channel blockers and therefore it will be a considerable advantage to identify clinically well-tolerated antagonists where such side effects are minimised. Porter and Greenamyre (J. Neurochem. 1995, 64, 614–623; incorporated herein by reference) demonstrated that well-tolerated and psychotomimetic NMDA receptor channel blockers could be differentiated on the basis of their relative affinities for forebrain and cerebellar receptors irrespective of absolute affinities. Selectivity for cerebellar NMDA receptors over forebrain NMDA receptors is observed for well-tolerated compounds. The basis of this observation may be related to different populations of NMDA receptor subtypes in these brain regions.

The use of a number of the known NMDA antagonists such as Dizocilpine, PCP, Cerestat and Ketamine gives rise to a number of side effects which render these compounds unsuitable for use in treatment. In particular, administration of the compounds is associated with perceptual and cognitive disturbances of a kind that resemble naturally-occurring psychotic states.

In addition, the perceptual and cognitive side effects of the compounds become more pronounced after the onset of puberty and sexual maturation, and these compounds are therefore particularly unsuitable for the treatment of adults. This developmental change has been demonstrated empirically in both experimental animals and in man, and is paralleled in experimental animals by brain hypermetabolism.

In summary, there is a need for an NMDA antagonist which is well-tolerated and does not give rise to the side effects associated with previous clinically investigated NMDA antagonists.

SUMMARY OF THE INVENTION

A number of compounds have now been found that show affinity for the NMDA receptor and are useful in the treatment of conditions generally associated with abnormalities in glutamatergic transmission such as stroke, traumatic brain injury and neurodegenerative diseases such as Parkinson's and Alzheimer's diseases. It has also been found that the compounds have a surprisingly favourable ratio of cortex to cerebellar binding affinity which indicates that these compounds would be well-tolerated in vivo.

DETAILED DESCRIPTION OF PREFERRED EMBODIMENTS

According to the present invention there is provided the use of a compound of the formula (1):

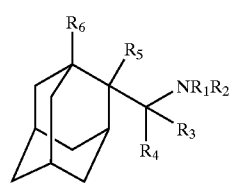

(1)

wherein $R_1$, $R_2$, $R_3$, $R_4$, $R_5$ and $R_6$ are independently selected from hydrogen, alkyl and aryl, or pharmaceutically acceptable salts thereof, with the proviso that wherein $R_1$ to $R_4$ and $R_6$ are hydrogen, $R_5$ is not selected from $CH_2CH_2NHSO_2CH_3$, $CH_2CH_2NHSO_2CF_3$ and methyl substituted by $SO_2NH_2$, $SO_3H$, $PO_3H_2$, $CONHOH$ or a heterocyclic group selected from

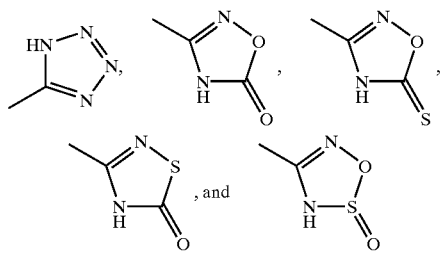

in the manufacture of a medicament for use in the treatment of a condition generally associated with abnormalities in glutamatergic transmission.

As used herein, the term "alkyl" means a branched or unbranched, cyclic or acyclic, saturated or unsaturated (e.g. alkenyl or alkynyl) hydrocarbyl radical which may be substituted or unsubstituted. Where cyclic, the alkyl group is preferably $C_3$ to $C_{12}$, more preferably $C_5$ to $C_{10}$, more preferably $C_5$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl.

As used herein, the term "aryl" means a substituted or unsubstituted carbocyclic aromatic group, such as phenyl or naphthyl, or a substituted or unsubstituted heteroaromatic group containing one or more, preferably one, heteroatom, such as pyridyl, pyrrolyl, furanyl, thienyl, thiazolyl, isothiazolyl, oxazolyl, isoxazolyl, oxadiazolyl, thiadiazolyl, pyrazolyl, imidazolyl, triazolyl, pyrimidinyl pyridazinyl, pyrazinyl, triazinyl, indolyl, indazolyl, quinolyl, quinazolyl, benzimidazolyl, benzothiazolyl, benzisoxazolyl and benzisothiazolyl. In one embodiment, the aryl group comprises phenyl.

The alkyl and aryl groups may be substituted or unsubstituted. Where substituted, there will generally be 1 to 3 substituents present, preferably 1 substituent. Substituents may include:

carbon-containing groups such as
  alkyl,
  aryl,
  arylalkyl (e.g. substituted and unsubstituted phenyl, substituted and unsubstituted benzyl);
halogen atoms and halogen-containing groups such as
  haloalkyl (e.g. trifluoromethyl);
oxygen-containing groups such as
  alcohols (e.g. hydroxy, hydroxyalkyl, aryl(hydroxy)alkyl),
  ethers (e.g. alkoxy, aryloxy, alkoxyalkyl, aryloxyalkyl),
  aldehydes (e.g. carboxaldehyde),
  ketones (e.g. alkylcarbonyl, alkylcarbonylalkyl, arylcarbonyl, arylalkylcarbon, arylcarbonylalkyl),
  acids (e.g. carboxy, carboxyalkyl),
  acid derivatives such as esters (e.g. alkoxycarbonyl, alkoxycarbonylalkyl, alkylcarbonyloxy, alkylcarbonyloxyalkyl),
  amides (e.g. aminocarbonyl, mono- or di-alkylaminocarbonyl, aminocarbonylalkyl, mono- or di-alkylaminocarbonylalkyl, arylaminocarbonyl), carbanates (e.g. alkoxycarbonylamino, aryloxycarbonylamino, aminocarbonyloxy, mono- or di-alkylaminocarbonyloxy, arylaminocarbonyloxy), and ureas (e.g. mono- or di-alkylaminocarbonylamino or arylaminocarbonylamino);

nitrogen-containing groups such as amines (e.g. amino, mono- or di-alkylamino, aminoalkyl, mono- or di-alkylaminoalkyl), azides, nitriles (e.g. cyano, cyanoalkyl), nitro;

sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl);

and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofiranyl, pyranyl, pyronyl, pyridyl, pyrazinyl, pyridazinyl, piperidyl, hexahydroazepinyl, piperazinyl, morpholinyl, benzothienyl, benzofuranyl, isobenzofuranyl, indolyl, oxyindolyl, isoindolyl, indazolyl, indolinyl, 7-azaindolyl, indolizinyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

As used herein, the term "alkoxy" means alkyl-O— and "alkoyl" means alkyl-CO— where alkyl is as previously defined.

As used herein, the term "halogen" means a fluorine, chlorine, bromine or iodine radical, preferably a fluorine, chlorine or bromine radical.

As used herein the term "conditions generally associated with abnormalities in glutamatergic transmission" primarily includes ischaemic stroke, haemorrhagic stroke, subarrachnoid haemorrhage, subdural haematoma, coronary artery bypass surgery, neurosurgery, traumatic brain injury, traumatic spinal injury, Alzheimer's disease, Parkinson's disease, Huntington's disease, Pick's disease, Lewy body disease, senile dementia, spongiform encephalopathies, prion-protein induced neurotoxicity, peri-natal asphyxia, demyelinating disease, multiinfarct dementia, vascular dementia, dementia pugilans, drug dependence, alcohol withdrawal, opiate withdrawal, motor neurone disease, multiple sclerosis, acute and chronic pain including neuropathic pain, cancer pain, trigeminal neuralgia, migraine, primary and secondary hyperalgesia, inflammatory pain, nociceptive pain, tabes dorsalis, phantom limb pain, spinal cord injury pain, central pain, post-herpetic pain, HIV pain and diabetic neuropathy. In addition, the term also includes the following conditions: epilepsy, AIDS dementia, multiple system atrophy, progressive supra-nuclear palsy, Friedrich's ataxia, autism, fragile X syndrome, tuberous sclerosis, attention deficit disorder, olivio-ponto-cerebellar atrophy, cerebral palsy, drug-induced optic neuritis, peripheral neuropathy, myelopathy, ischaemic retinopathy, glaucoma, cardiac arrest, meningitis, encephalitis, depression, bi-polar disorder, schizophrenia, psychosis, behaviour disorders, impulse control disorders, pre-eclampsia, neuroleptic malignant syndrome, chronic fatigue syndrome, anorexia nervosa, anxiety disorders, generalised anxiety disorder, panic disorder, phobias, fresh water drowning and decompression.

As used herein, the term "treatment" includes prophylactic treatment.

As used herein, the term "pharmaceutically acceptable salt" means any pharmaceutically acceptable salt of the compound of formula (1). Salts may be prepared from pharmaceutically acceptable non-toxic acids including inorganic and organic acids. Such acids include acetic, benzenesulfonic, benzoic, camphorsulfonic, citric, dichloroacetic, ethenesulfonic, fumaric, gluconic, glutamic, hippuric, hydrobromic, hydrochloric, isethionic, lactic, maleic, malic, mandelic, methanesulfonic, mucic, nitric, pamoic, pantothenic, phosphoric, succinic, sulfuric, tartaric, oxalic, p-toluenesulfonic and the like. Particularly preferred are hydrochloric, hydrobromic, phosphoric, fumaric, succinic, methanesulphonic and sulfuric acids, and most particularly preferred is the hydrochloride salt.

The compounds of formula (1) may exist in a number of diastereomeric and/or enantiomeric forms. Reference in the present specification to "a compound of formula (1)" is a reference to all stereoisomeric forms of the compound and includes a reference to the unseparated stereoisomers in a mixture, racemic or non-racemic, and to each stereoisomer in its optically pure form.

The compounds of the present invention are active as NMDA antagonists and are well-tolerated in that side-effects are minimised. Experimental data are shown in Table 1.

In the compounds of formula (1), preferably one or more of $R_1$, $R_2$, $R_3$, $R_4$ and $R_6$ are hydrogen. In a preferred embodiment of the present invention, one or both of $R_1$ and $R_2$ are hydrogen. In a further preferred embodiment, one or both of $R_3$ and $R_4$ are hydrogen. In a further preferred embodiment all of $R_1$, $R_2$, $R_3$, $R_4$, and $R_6$ are hydrogen.

In the compounds of formula (1), preferably $R_5$ is alkyl or aryl, more preferably $R_5$ is aryl.

Where $R_5$ is alkyl, preferably $R_5$ is an acyclic hydrocarbyl radical, preferably saturated, preferably unbranched and preferably unsubstituted. In one embodiment, $R_5$ is alkyl substituted by a substituted or unsubstituted carbocyclic aromatic group, preferably a phenyl group, or a substituted or unsubstituted heteroaromatic group containing 1 or 2, preferably 1, heteroatom and preferably a thienyl, pyridyl or furanyl group.

Where $R_5$ is aryl, preferably $R_5$ is a substituted or unsubstituted carbocyclic aromatic group or a substituted or unsubstituted heteroaromatic group containing 1 or 2 heteroatoms, preferably one heteroatom. More preferably, $R_5$ is a carbocyclic aromatic group, preferably phenyl, substituted or unsubstituted. Where substituted, $R_5$ is preferably mono-substituted. Where $R_5$ is a mono-substituted phenyl group, the substituent is preferably in the meta or para position, and more preferably the meta position, of the phenyl ring with respect to the adamantane group. Preferred substituents are selected from $C_1$ to $C_4$ alkyl, preferably methyl and ethyl; halogen, preferably fluorine and chlorine; alkoxy, preferably methoxy; and haloalkyl, preferably trifluoromethyl. Preferably $R_5$ is selected from phenyl, 3-methylphenyl, 4-methylphenyl and 3-ethylphenyl. More preferably $R_5$ is selected from 3-methylphenyl and 3-ethylphenyl. Most preferably $R_5$ is 3-methylphenyl. In the embodiment where $R_5$ is a heteroaromatic group, it is preferred that $R_5$ is selected from thienyl, pyridyl and furanyl groups, most preferably thienyl, substituted or unsubstituted.

In one embodiment of the invention, the compounds are selected from compounds other than those wherein $R_1$, $R_2$, $R_3$, $R_4$ and $R_6$ are hydrogen and $R_5$ is either $C_{1-2}$ alkyl substituted by sulfonamide, amide, phosphonic acid, sulfonic acid, hydroxamic acid or a heterocyclic group or $R_5$ is a heterocyclic group, particularly wherein said heterocyclic group is a heteroaromatic group, and particularly wherein the heterocyclic group contains 3 or more heteroatoms.

In a further embodiment of the invention, the compounds are selected from compounds other than those wherein $R_1$, $R_2$, $R_3$, $R_4$ and $R_6$ are hydrogen and $R_5$ comprises a group which is a sulfonamide, amide, phosphonic acid, sulfonic acid, hydroxamic acid or a heterocyclic group, particularly wherein said heterocyclic group is a heteroaromatic group, and particularly wherein said heterocyclic group contains 3 or more heteroatoms.

In an alternative embodiment of the invention, the compounds are selected from compounds other than those wherein $R_1$, $R_2$, $R_3$, $R_4$ and $R_6$ are hydrogen and $R_5$ is not selected from $CH_2CH_2NHSO_2CH_3$, $CH_2CH_2NHSO_2CF_3$ and methyl substituted by $SO_2NH_2$, $SO_3H$, $PO_3H_2$, CONHOH or a heterocyclic group selected from tetrazol-5-yl, 5-oxo-4H-[1,2,4]oxadiazol-3-yl, 5-thioxo-4H-[1,2,4]oxadiazol-3-yl, 5-oxo-4H-[1,2,4]thiadiazol-3-yl and 2-oxo-2,3-dihydro-[1,2,3,5]oxathiadiazol-4-yl. In a further alternative embodiment of the invention, the compounds are selected from compounds other than those wherein $R_1$, $R_2$, $R_3$, $R_4$ and $R_6$ are hydrogen and $R_5$ comprises a group which is a sulfonamide, amide, phosphonic acid, sulfonic acid, hydroxamic acid or a heterocyclic group selected from tetrazol-5-yl, 5-oxo-4H-[1,2,4]oxadiazol-3-yl, 5-thioxo-4H-[1,2,4]oxadiazol-3-yl, 5-oxo-4H-[1,2,4]thiadiazol-3-yl and 2-oxo-2,3-dihydro-[1,2,3,5]oxathiadiazol-4-yl.

Particularly preferred compounds are 2-(3-ethylphenyl)-2-adamantanemethanamine, 2-(3-methylphenyl)-2-adamantanemethanamine, 2-phenyl-2-adamantanemethanamine and 2-(4-methylphenyl)-2-adamantanemethanamine, and the hydrochloride salts thereof.

The present invention further provides a method of treatment of conditions generally associated with abnormalities in glutamatergic transmission comprising administering to a patient an effective dose of a compound of formula (1) as defined above, or pharmaceutically acceptable salts thereof.

The present invention also provides, for use in therapy, a compound of formula (1) as defined above and pharmaceutically acceptable salts thereof, other than compounds in which $R_3$, $R_4$, $R_5$ and $R_6$ are hydrogen and one of $R_1$ and $R_2$ is hydrogen, methyl or benzyl and one of $R_1$ and $R_2$ is a substituted methyl, ethyl or propyl group, and other than the compounds in which $R_1$, $R_2$, $R_5$ and $R_6$ are hydrogen and $R_3$ and $R_4$ are selected from methyl and aminomethyl.

In a preferred embodiment, the present invention provides, for use in therapy, compounds of formula (1) as defined above and pharmaceutically acceptable salts thereof, other than compounds in which $R_3$, $R_4$, $R_5$ and $R_6$ are hydrogen and $R_1$ and $R_2$ are independently selected from alkyl and other than compounds in which $R_1$, $R_2$, $R_5$ and $R_6$ are hydrogen and $R_3$ and $R_4$ are independently selected from alkyl.

In an alternative preferred embodiment, the present invention provides, for use in therapy, compounds of formula (1) as defined above and pharmaceutically acceptable salts thereof, wherein (i) $R_3$, $R_4$, $R_5$ and $R_6$ are independently selected from hydrogen, alkyl and aryl and $R_1$ and $R_2$ are independently selected from hydrogen and aryl; or (ii) $R_3$, $R_4$, $R_5$ and $R_6$ are independently selected from alkyl and aryl and $R_1$ and $R_2$ are independently selected from alkyl; or (iii) $R_1$, $R_2$, $R_5$ and $R_6$ are independently selected from hydrogen, alkyl and aryl and $R_3$ and $R_4$ are independently selected from hydrogen and aryl; or (iv) $R_1$, $R_2$, $R_5$ and $R_6$ are independently selected from alkyl and aryl and $R_3$ and $R_4$ are independently selected from alkyl.

In a further preferred embodiment, the present invention provides, for use in therapy, compounds of formula (1) as defined above and pharmaceutically acceptable salts thereof, wherein $R_5$ and $R_6$ are independently selected from alkyl and aryl.

In a particularly preferred embodiment, the present invention provides, for use in therapy, compounds of formula (1) as defined above and pharmaceutically acceptable salts thereof, wherein $R_5$ is selected from alkyl and aryl.

The present invention also provides a compound of the formula (1) as defined above and pharmaceutically acceptable salts thereof, wherein $R_5$ is selected from alkyl and aryl, with the proviso that where $R_1$ and $R_2$ are methyl and $R_3$, $R_4$ and $R_6$ are hydrogen, $R_5$ is not hydroxymethyl.

According to a further aspect of the present invention there is provided a method of preparing the compounds of the formula (1) as defined above wherein $R_5$ is selected from alkyl and aryl, other than the compounds in which $R_1$ and $R_2$ are methyl, $R_3$, $R_4$ and $R_6$ are hydrogen and $R_5$ is hydroxymethyl.

Compounds of formula (1) may be prepared by conventional synthetic routes, for example compounds where $R_1$, $R_2$, $R_3$ and $R_4$ are all hydrogen may be prepared as illustrated in Reaction Scheme 1.

Reaction Scheme 1

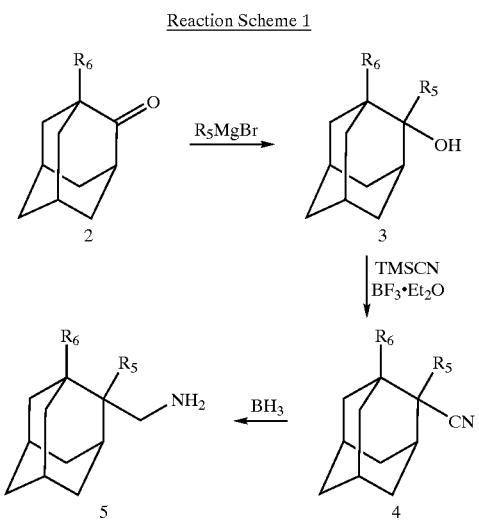

Amines (5) are prepared by reduction of the corresponding nitrile (4) by standard methods such as borane. Nitriles (4) are prepared from alcohols (3) by standard methods such as TMSCN in the presence of $BF_3$. Alcohols (3) are prepared by addition of, for example, Grignard reagents to the corresponding 2-adamantanones (2) which may be available commercially or are synthesised by standard methods.

Compounds of formula (1) where $R_1$ and/or $R_2$ are alkyl may be prepared from amines (5) by standard methods including alkylation, reductive alkylation or acylation/reduction.

Compounds of formula (1) where $R_1$ and/or $R_2$ are aryl may be prepared from amines (5) by standard methods such as palladium-catalysed coupling to aryl halides.

Compounds of formula (1) where $R_3$ and/or $R_4$ are alkyl or aryl may be prepared from nitriles (4) by standard methods such as the addition of metallated alkyl or aryl anions.

Compounds of formula (1) where $R_1$, $R_2$, $R_3$ and $R_4$ are not all hydrogen may also be prepared as illustrated in Reaction Scheme 2.

Reaction Scheme 2

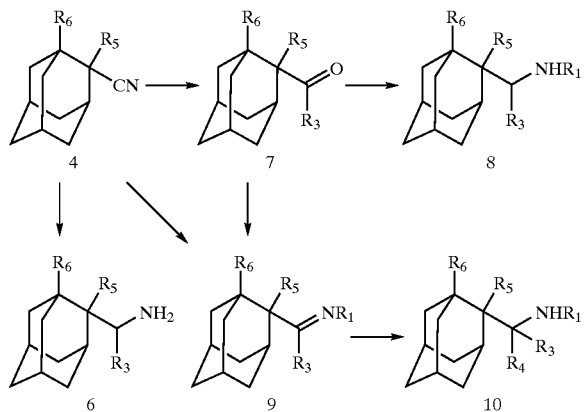

Amines (6) where $R_3$ is alkyl or aryl may be prepared from nitriles (4) by standard methods such as addition of a metallated alkyl or aryl anion followed by reduction.

Amines (8) where $R_3$ is hydrogen, alkyl or aryl may be prepared from ketones (7) by standard methods such as reductive amination. Ketones (7) where $R_3$ is alkyl or aryl may be prepared from nitriles (4) by standard methods such as addition of a metallated alkyl or aryl anion followed by hydrolysis. Ketones (7) where $R_3$ is hydrogen may be prepared from nitriles (4) by standard methods such as reduction.

Amines (10) where $R_3$ and $R_4$ are alkyl or aryl may be prepared from i mines (9) by standard methods such as addition of a Grignard reagent. Amines (10) may be converted to further compounds of formula (1) as described above. Imines (9) where $R_3$ is alkyl or aryl and $R_1$ is alkyl or aryl may be prepared from ketones (7) by standard methods such as treatment with an amine. Alternatively imines (9) where $R_1$ is alkyl may be prepared from nitriles (4) by addition of a metallated alkyl or aryl anion followed by treatment, for example, with an alkyl halide.

The present invention further provides a pharmaceutical composition comprising the compound of the formula (1), or a pharmaceutically acceptable salt thereof, in combination with a pharmaceutically acceptable excipient.

The compound of formula (1) may be administered in a form suitable for oral use, for example a tablet, capsule, pellet, aqueous or oily solution, suspension or emulsion; for topical use including transmucosal and transdermal use, for example a cream, ointment, gel, aqueous or oil solution or suspension, salve, patch or plaster; for nasal use, for a example a snuff, nasal spray, nasal powder or nasal drops; for vaginal or rectal use, for example a suppository or pessary; for administration by inhalation, for example a finely divided powder or a liquid aerosol; for sub-lingual or buccal use, for example a tablet or capsule for ocular use, for example a sterile aqueous solution or sterile ointment; or for parenteral use (including intravenous, subcutaneous, intramuscular, intravascular or infusion), for example a sterile aqueous or oil solution or suspension or emulsion, or depot injection formulation. In general the above compositions may be prepared in a conventional manner using conventional excipients, using standard techniques, including controlled release technologies, such as gelatin, lipid, gel depot, liposome and microcapsule based systems well known to those skilled in the art of pharmacy.

For oral administration, the compounds of the invention will generally be provided in the form of tablets or capsules or as an aqueous solution or suspension.

Tablets or pellets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, calcium hydrogen phosphate, cellulose derivatives, and lactose, while corn starch and alginic acid are suitable disintegrating agents. Binding agents may include starch, gelatin and polyvinyl-pyrrolidone derivatives, while the lubricating agent, if present, will generally be magnesium stearate, stearic acid or talc. If desired, the tablets may be formulated or coated with a material such as glyceryl monostearate or glyceryl distearate or polymethacrylate polymers, cellulose derivatives or other pharmaceutically acceptable polymer, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions or emulsions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Transdermal formulations include membrane permeation systems, multi-laminate adhesive dispersion systems and matrix dispersion systems. Transdermal delivery also includes the use of electrically aided transport and skin penetration enhancers and needle-free injection devices.

The preferred route of administration will be as an intravenous infusion, preferably over a period of up to seven days, or as an oral formulation, or as an intramuscular injection via a styrette or as a subcutaneous injection.

It will be appreciated that the dosage levels used may vary over quite a wide range depending upon the compound used, the severity of the condition exhibited by the patient and the patient's body weight. However, without commitment to a rigid definition of dosages it may be stated that a daily dosage of the active constituent (estimated as the free base) is 100 μg to 800 mg. More particularly the preferred compounds may be administered at a preferred dose of 50–800 mg daily in single or divided doses.

The invention will now be described in detail. It will be appreciated that the invention is described by way of example only and modification of detail may be made without departing from the scope of the invention.

EXPERIMENTAL

I. Synthesis

EXAMPLE 1

2-(3-Ethylphenyl)-2-adamantanemethanamine hydrochloride

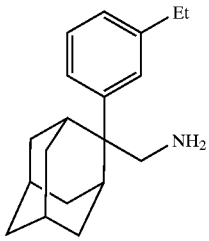

2-(3-Ethylphenyl)-2-adamantanol

A stirring mixture of magnesium turnings (0.89 g, 36.6 mmol) and iodine (catalytic) in dry THF (60 mL) was treated with 3-bromoethylbenzene (5 mL, 36.6 mmol), refluxed for 3 h, cooled to room temperature, treated with a solution of 2-adamantanone (5.0 g, 33.3 mmol) in dry THF (20 mL) and refluxed for 2 h. The mixture was cooled to room temperature, treated with 3-M HCl (20 mL), extracted with EtOAc (2×20 mL), the combined extracts were washed with water (10 mL), dried ($MgSO_4$), concentrated in vacuo and purified by chromatography [$SiO_2$; heptane-EtOAc (9:1)] to give the product (7.84 g, 92 %) as a white solid: mp 63–65° C.; IR $v_{max}$ (Nujol)/cm$^{-1}$ 3442, 3281, 2921, 2855, 1604, 1451, 1101, 1043, 1009, 803 and 708; NMR $\delta_H$ (400 MHz, $CDCl_3$) 1.23 (3H, t, J 7.5 Hz), 1.61–1.70 (9H, m), 1.89 (1H, s), 2.38–2.41 (2H, m), 2.56 (2H, s), 2.65 (2H, q, J 7.5 Hz), 3.46 (1H, s), 7.11 (1H, d, J 7.5 Hz) and 7.24–7.36 (3H, m); Anal. Calcd for $C_{18}H_{24}O$: C, 84.32; H, 9.43. Found: C, 84.24; H, 9.28.

2-(3-Ethylphenyl)-2-adamantanecarbonitrile

A solution of 2-(3-ethylphenyl)-2-adamantanol (1.82 g, 7.14 mmol) in dry $CHCl_3$ (5 mL) under argon, was treated with trimethylsilyl cyanide (1.00 mL, 7.5 mmol), cooled to 0° C., treated with $BF_3$ etherate (1.10 mL, 8.57 mmol), allowed to warm to room temperature and stirred for 2 h. The mixture was treated with dilute $NaHCO_3$ (10 mL), extracted with $CHCl_3$ (2×10 mL), the combined extracts washed with water (10 mL), dried ($MgSO_4$), concentrated in vacuo and purified by chromatography [$SiO_2$; heptane-EtOAc (9:1)] to give the product (1.54 g, 82%) as a colourless oil: IR $v_{max}$ (thin film)/cm$^{-1}$ 2922, 2860, 2226, 1604, 1487, 1453, 1105, 799 and 704; NMR $\delta_H$ (400 MHz, $CDCl_3$) 1.24 (3H, t, J 7.5 Hz), 1.62–1.65 (2H, m), 1.70–1.82 (5H, m), 1.98–204 (3H, m), 2.45–2.48 (2H, m), 2.66 (2H, q, J 7.5 Hz), 2.79 (2H, s), 7.15 (1H, d, J 7.5 Hz) and 7.25–7.34 (3H, m); Anal. Calcd for $C_{19}H_{23}N$: C, 85.99; H, 8.73; N, 5.28. Found: C, 85.85; H, 8.77; N, 5.23.

2-(3-Ethylphenyl)-2-adamantanemethanamine hydrochloride

A solution of 2-(3-ethylphenyl)-2-adamantanecarbonitrile (265 mg, 1 mmol) in dry THF (5 mL) under argon was treated with 1-M $BH_3$ in THF (3.3 mL, 3.3 mmol), refluxed for 2 h, cooled to room temperature, treated with 6-M HCl (10 mL), refluxed for 0.25 h, cooled to room temperature and extracted with $CHCl_3$ (2×10 mL). The combined extracts were washed with water (2×5 mL), dried ($MgSO_4$), concentrated in vacuo and purified by chromatography [$SiO_2$; EtOAc-MeOH (9:1)] to give the title compound (258 mg, 85%) as a white solid: mp 89–90° C.; IR $v_{max}$ (Nujol)/cm$^{-1}$ 3395, 2922, 1603, 1489, 1458, 1376, 1100, 797, 734 and 713; NMR $\delta_H$ (400 MHz, DMSO-$d_6$) 1.19 (3H, d, J 7.5 Hz), 1.41–1.57 (2H, m), 1.60–1.75 (6H, m), 1.89 (1H, s), 2.06–2.15 (2H, m), 2.46–2.64 (5H, m), 3.05 (2H, s) and 7.02–7.33 (7H, m); Anal. Calcd for $C_{19}H_{28}ClN.0.2 H_2O$: C, 73.74; H, 9.25; N, 4.53. Found: C, 73.90; H, 9.28; N, 4.53.

EXAMPLE 2

2-(3-Methylphenyl)-2-adamantanemethanamine hydrochloride

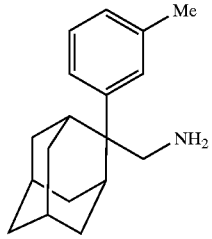

2-(3-Methylphenyl)-2-adamantanecarbonitrile

This was prepared by the method of example 1 using 2-(3-methylphenyl)-2-adamantanol in place of 2-(3-ethylphenyl)-2-adamantanol and the product (1.16 g, 66%) isolated as a white solid: mp 85–86° C.; IR $v_{max}$ (Nujol)/cm$^{-1}$ 2924, 2858, 2225, 1604, 1455, 1378, 1103, 783 and 705; NMR $\delta_H$ (400 MHz, $CDCl_3$) 1.63–1.66 (2H, m), 1.76–1.82 (5H, m), 1.99–2.05 (3H, m), 2.38 (3H, s), 2.45–2.48 (2H, m), 2.78 (2H, s), 7.10 (1H, d, J 8.0 Hz) and 7.26–7.30 (3H, m); Anal. Calcd for $C_{18}H_{21}N$: C, 86.01; H, 8.42; N, 5.57. Found: C, 85.82; H, 8.50; N, 5.54.

2-(3-Methylphenyl)-2-adamantanemethanamine hydrochloride

This was prepared by the method of example 1 using 2-(3-methylphenyl)-2-adamantanecarbonitrile in place of 2-(3-ethylphenyl)-2-adamantanecarbonitrile and the title compound (261 mg, 90%) isolated as a white solid: mp 242–243° C.; IR $v_{max}$ (Nujol)/cm$^{-1}$ 2923, 1591, 1511, 1493, 1457, 1376, 1355, 1130, 1099, 778 and 710; NMR $\delta^H$ (400 MHz, DMSO-$d_6$) 1.52 (2H, d, J 11.5 Hz), 1.64–1.72 (7H, m), 1.89 (1H, s) 2.10 (2H, d, J11.5 Hz), 2.31 (3H, s), 2.53 (2H, s), 3.06 (2H, s), 7.07 (1H, d, J 7.5 Hz) 7.14–7.18 (2H, m), 7.26–7.28 (1H, m) and 7.50 (3H, br s); Anal. Calcd for $C_{18}H_{26}ClN$: C, 74.08; H, 8.98; N, 4.80. Found: C, 73.97; H, 9.14; N, 4.80.

EXAMPLE 3

2-Phenyl-2-adamantanemethanamine hydrochloride

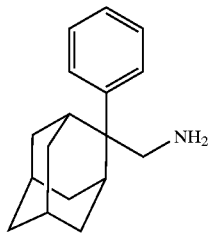

2-Phenyl-2-adamantanecarbonitrile

This was prepared by the method of example 1 using 2-phenyl-2-adamantanol in place of 2-(3-ethylphenyl)-2-adamantanol and the product (900 mg, 97%) isolated as a white solid: mp 120–122° C.; IR $v_{max}$ (Nujol)/cm$^{-1}$ 2924, 2852, 2221, 1598, 1494, 1453, 1376, 1363, 1108, 761 and 704; NMR $\delta_H$ (400 MHz, CDCl$_3$) 1.65 (2H, m), 1.73–1.83 (5H, m), 2.04 (3H, m), 2.48 (2H, m), 2.80 (2H, s), 7.32 (1H, m), 7.42 (2H, m) and 7.47 (2H, m); Anal. Calcd for $C_{17}H_{19}N$: C, 86.03; H, 8.07; N, 5.90. Found: C, 85.89; H, 8.15; N, 5.85.

2-Phenyl-2-adamantanemethanamine hydrochloride

This was prepared by the method of example 1 using 2-phenyl-2-adamantanecarbonitrile in place of 2-(3-ethylphenyl)-2-adamantanecarbonitrile and the title compound (249 mg, 90%) isolated as a white solid: mp 253–255° C.; IR $v_{max}$ (Nujol)/cm$^{-1}$ 2920, 1593, 1498, 1458, 1377, 1097, 761 and 698; NMR $\delta_H$ (400 MHz, DMSO-d$_6$) 1.52 (2H, d, J 12.5 Hz), 1.64–1.72 (7H, m), 1.89 (1H, s), 2.10 (2H, d, J 12.5 Hz), 2.48 (3H, s), 3.05 (2H, s), 7.0 (3H, br s), 7.23 (1H, m) and 7.36–7.41 (3H, m); Anal. Calcd for $C_{17}H_{24}ClN$: C, 73.49; H, 8.71; N, 5.04. Found: C, 73.73; H, 8.82; N, 5.05.

EXAMPLE 4

2-(4-Methylphenyl)-2-adamantanemethanamine hydrochloride

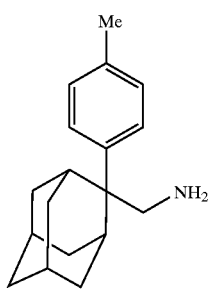

2-(4-Methylphenyl)-2-adamantanecarbonitrile

This was prepared by the method of example 1 using 2-(4-methylphenyl)-2-adamantanol in place of 2-(3-ethylphenyl)-2-adamantanol and the product (933 mg, 54%) isolated as a white crystalline solid: mp 99–100° C.; IR $v_{max}$ (Nujol)/cm$^{-1}$ 2921, 2855, 2221, 1514, 1453, 1377, 1194, 1100 and 813; NMR $\delta_H$ (400 MHz, CDCl$_3$) 1.64 (2H, d, J 13 Hz), 1.76–1.82 (5H, m), 1.99–2.05 (3H, m), 2.36 (3H, s), 2.46 (2H, d, J 13 Hz), 2.77 (2H, s), 7.23 (2H, d, J 8 Hz) and 7.36 (2H, d, J 8 Hz); Anal. Calcd for $C_{18}H_{21}N$: C, 86.01; H, 8.42; N, 5.57. Found: C, 86.11; H, 8.48; N, 5.57.

2-(4-Methylphenyl)-2-adamantanemethanamine hydrochloride

This was prepared by the method of example 1 using 2-(4-methylphenyl)-2-adamantanecarbonitrile in place of 2-(3-ethylphenyl)-2-adamantanecarbonitrile and the title compound (261 mg, 90%) isolated as a white solid: mp 261–263° C.; IR $v_{max}$ (Nujol)/cm$^{-1}$ 3408, 3259, 2923, 1603, 1501, 1457, 1377, 1096 and 812; NMR $\delta_H$ (400 MHz, DMSO-d$_6$) 1.48–1.51 (2H, m), 1.63–1.71 (7H, m), 1.88 (1H, br s), 2.07–2.10 (2H, m), 2.28 (3H, s), 2.48 (2H, m), 3.04 (2H, s), 7.15–7.30 (4H, m) and 7.41 (3H, br s); Anal. Calcd for $C_{18}H_{26}ClN \cdot 0.85 H_2O$: C, 70.38; H, 9.09; N, 4.56. Found: C, 70.41; H, 8.87; N, 4.44.

EXAMPLE 5

2-(2-Methylphenyl)-2-adamantanemethanamine hydrochloride

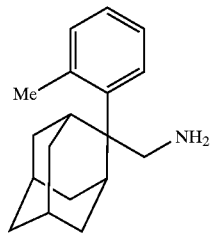

2-(2-Methylphenyl)-2-adamantanecarbonitrile

This was prepared by the method of example 1 using 2-(2-methylphenyl)-2-adamantanol in place of 2-(3-ethylphenyl)-2-adamantanol and the product (580 mg, 34%) isolated as a white solid: mp 80–81° C.; IR $v_{max}$ (Nujol)/cm$^{-1}$ 2922, 2854, 2220, 1487, 1451, 1378, 1365, 762 and 729; NMR $\delta_H$ (400 MHz, CDCl$_3$) 1.59–1.77 (6H, m), 1.97–2.03 (4H, m), 2.51–2.60 (5H, m), 2.90 (2H, br s), 7.21–7.26 (3H, m) and 7.40–7.43 (1H, m); Anal. Calcd for $C_{18}H_{21}N$: C, 86.01; H, 8.42; N, 5.57. Found: C, 85.97; H, 8.48; N, 5.56.

2-(2-Methylphenyl)-2-adamantanemethanamine hydrochloride

This was prepared by the method of example 1 using 2-(2-methylphenyl)-2-adamantanecarbonitrile in place of 2-(3-ethylphenyl)-2-adamantanecarbonitrile and the title compound (174 mg, 60%) isolated as a white solid: mp 270–271° C.; IR $v_{max}$ (Nujol)/cm$^{-1}$ 2921, 1592, 1487, 1459, 1377, 759 and 733; NMR $\delta_H$ (400 MHz, DMSO-d$_6$) 1.43 (1H, d, J 12.5 Hz), 1.55–1.76 (7H, m), 1.86 (2H, s), 2.11–2.16 (2H, m), 2.41 (3H, s), 2.69 (1H, s), 2.83 (1H, s), 2.95 (1H, d, J 12.5 Hz), 3.44 (1H, d, J 13.0 Hz), 6.90 (3H, br s) and 7.10–7.34 (4H, m); Anal. Calcd for $C_{18}H_{26}ClN$: C, 74.08; H, 8.98; N, 4.80. Found: C, 74.48; H, 9.07; N, 4.79.

EXAMPLE 6

2-(4-Fluorophenyl)-2-adamantanemethanamine hydrochloride

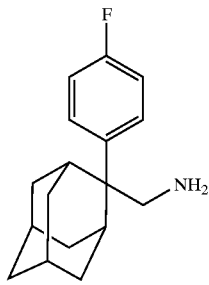

2-(4-Fluorophenyl)-2-adamantanecarbonitrile

This was prepared by the method of example 1 using 2-(4-fluorophenyl)-2-adamantanol in place of 2-(3-ethylphenyl)-2-adamantanol and the product (163 mg, 64%) isolated as a white solid: mp 81–82° C.; IR $v_{max}$ (Nujol)/cm$^{-1}$ 2924, 2861, 2223, 1601, 1510, 1502, 1467, 1454, 1242, 1166, 1104 and 835; NMR $\delta_H$ (400 MHz, CDCl$_3$) 1.62–1.65 (2H, m), 1.74 (5H, s), 1.97–2.03 (3H, m), 2.44 (2H, d, J 12.5 Hz), 2.73 (2H, s), 7.07–7.11 (2H, m) and 7.41–7.44 (2H, m); Anal. Calcd for C$_{17}$H$_{18}$FN: C, 79.97; H, 7.11; N, 5.48. Found: C, 80.02; H, 7.21; N, 5.47.

2-(4-Fluorophenyl)-2-adamantanemethanamine hydrochloride

This was prepared by the method of example 1 using 2-(4-fluorophenyl)-2-adamantanecarbonitrile in place of 2-(3-ethylphenyl)-2-adamantanecarbonitrile and the title compound (251 mg, 85%) isolated as a white solid: mp 262–263° C.; IR $v_{max}$ (Nujol)/cm$^{-1}$ 2923, 2855, 1605, 1511, 1458, 1377, 1237, 1213, 1164 and 826; NMR $\delta_H$ (400 MHz, DMSO-d$_6$) 1.50–1.74 (9H, m), 1.90 (1H, s), 2.09–2.14 (2H, m), 2.46–2.56 (2H, m), 3.04 (2H, s), 7.01 (3H, br s), 7.10–7.21 (2H, m) and 7.30–7.40 (2H, m); Anal. Calcd for C$_{17}$H$_{23}$ClFN: C, 69.02; H, 7.84; N, 4.73. Found: C, 68.89; H, 7.93; N, 4.67.

EXAMPLE 7

2-(4-Chlorophenyl)-2-adamantanemethanamine hydrochloride

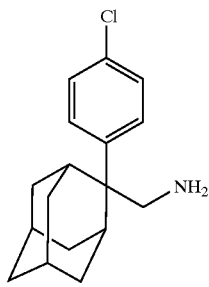

2-(4-Chlorophenyl)-2-adamantanecarbonitrile

This was prepared by the method of example 1 using 2-(4-chlorophenyl)-2-adamantanol in place of 2-(3-ethylphenyl)-2-adamantanol and the product (1.15 g, 60%) isolated as a white solid: mp 131.5–133° C.; IR $v_{max}$ (Nujol)/cm$^{-1}$ 2926, 2852, 2223, 1490, 1454, 1401, 1108, 1092, 1015 and 824; NMR $\delta_H$ (400 MHz, CDCl$_3$) 1.63–1.76 (7H, m), 1.99–2.05 (3H, m), 2.02–2.05 (2H, m), 2.74 (2H, s) and 7.38–7.42 (4H, m); Anal. Calcd for C$_{17}$H$_{18}$ClN: C, 75.13; H, 6.68; N, 5.15. Found: C, 74.96; H, 6.71; N, 5.13.

2-(4-Chlorophenyl)-2-adamantanemethanamine hydrochloride

This was prepared by the method of example 1 using 2-(4-chlorophenyl)-2-adamantanecarbonitrile in place of 2-(3-ethylphenyl)-2-adamantanecarbonitrile and the title compound (280 mg, 90%) isolated as a white solid: mp >300° C.; IR $v_{max}$ (Nujol)/cm$^{-1}$ 2927, 1517, 1509, 1494, 1455, 1377, 1102, 1092, 1010, 974, 821 and 720; NMR $\delta_H$ (400 MHz, DMSO-d$_6$) 1.52–1.77 (7H, m), 1.90 (1H, s), 2.10–2.13 (2H, m), 2.51–2.56 (3H, m), 3.10 (2H, br s), 3.65–3.67 (1H, m), 7.39–7.46 (4H, m) and 7.58–7.64 (3H, m); Anal. Calcd for C$_{17}$H$_{23}$Cl$_2$N: C, 65.39; H, 7.42; N, 4.48. Found: C, 65.11; H, 7.46; N, 4.40.

EXAMPLE 8

2-(4-Methoxyphenyl)-2-adamantanemethanamine hydrochloride

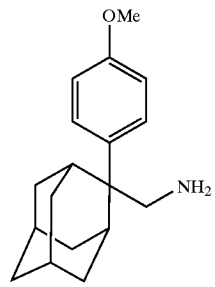

2-(4-Methoxyphenyl)-2-adamantanecarbonitrile

This was prepared by the method of example 1 using 2-(4-methoxyphenyl)-2-adamantanol in place of 2-(3-ethylphenyl)-2-adamantanol and the product (601 mg, 58%) isolated as a pale yellow solid: mp 165–166.5° C.; IR $\delta_{max}$ (Nujol)/cm$^{-1}$ 2918, 2855, 2220, 1609, 1512, 1458, 1377, 1298, 1260, 1183 and 1029; NMR $v_H$ (400 MHz, CDCl$_3$) 1.63 (2H, d, J 13.0 Hz), 1.75–1.81 (5H, m), 1.98–2.04 (3H, m), 2.45 (2H, J 13.0 Hz), 2.74 (2H, s), 3.82 (3H, s), 6.94 (2H, d, J 8.5 Hz) and 7.38 (2H, d, J 8.5 Hz); Anal. Calcd for C$_{18}$H$_{21}$NO: C, 80.86; H, 7.92; N, 5.24. Found: C, 80.60; H, 7.94; N, 5.20.

2-(4-Methoxyphenyl)-2-adamantanemethanamine hydrochloride

This was prepared by the method of example 1 using 2-(4-methoxyphenyl)-2-adamantanecarbonitrile in place of 2-(3-ethylphenyl)-2-adamantanecarbonitrile and the title compound (215 mg, 70%) isolated as a white solid: mp 234–235° C.; IR $v_{max}$ (Nujol)/cm$^{-1}$ 2922, 2854, 1610, 1515, 1465, 1377, 1259, 1188 and 1040; NMR $\delta_H$ (400 MHz, DMSO-d$_6$) 1.50 (2H, d, J 12.0 Hz), 1.63–1.71 (7H, m), 1.88 (1H, br s), 2.09 (2H, d, J 12.0 Hz), 2.49–2.50 (2H, m), 3.04 (2H, s), 3.74 (3H, s), 6.92 (2H, d, J 8.5 Hz), 7.24 (2H, d, J 8.5 Hz) and 7.55 (3H, br s); Anal. Calcd for C$_{18}$H$_{26}$ClNO: C, 70.23; H, 8.51; N, 4.55. Found: C, 70.06; H, 8.74; N, 4.45.

EXAMPLE 9

2-(4-Trifluoromethylphenyl)-2-adamantanemethanamine hydrochloride

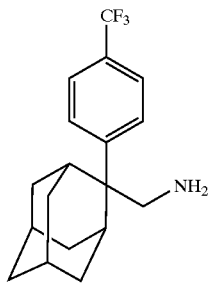

2-(4-Trifluoromethylphenyl)-2-adamantanecarbonitrile

This was prepared by the method of example 1 using 2-(4-trifluoromethylphenyl)-2-adamantanol in place of 2-(3-ethylphenyl)-2-adamantanol and the product (1.0 g, 46%) isolated as a white solid: mp 122–123.5° C.; IR $v_{max}$ (Nujol)/cm$^{-1}$ 2924, 2855, 2227, 1615, 1455, 1328, 1309, 1166, 1124, 1069 and 832; NMR $\delta_H$ (400 MHz, CDCl$_3$) 1.70–1.78 (7H, m), 2.02–2.06 (3H, m), 2.47–2.50 (2H, m), 2.81 (2H, s), 7.62 (2H, d, J 8.5 Hz) and 7.69 (2H, d, J 8.5 Hz); Anal. Calcd for $C_{18}H_{18}F_3N$: C, 70.81; H, 5.94; N, 4.59. Found: C, 70.71; H, 5.97; N, 4.55.

2-(4-Trifluoromethylphenyl)-2-adamantanemethanamine hydrochloride

This was prepared by the method of example 1 using 2-(4-trifluoromethylphenyl)-2-adamantanecarbonitrile in place of 2-(3-ethylphenyl)-2-adamantanecarbonitrile and the title compound (310 mg, 90%) isolated as a white solid: mp 279–281° C.; IR $v_{max}$ (Nujol)/cm$^{-1}$ 2921, 1618, 1460, 1377, 1328, 1161, 1126, 1070, 1014 and 845; NMR $\delta^H$ (400 MHz, DMSO-d$_6$) 1.56–1.74 (9H, m), 1.80 (1H, br s), 2.10–2.14 (2H, m), 2.60 (2H, s), 3.13 (2H, s), 7.58–7.60 (5H, m) and 7.73–7.75 (2H, m); Anal. Calcd for $C_{18}H_{23}ClF_3N \cdot 0.75\ H_2O$: C, 60.16; H, 6.87; N, 3.90. Found: C, 60.09; H, 6.76; N, 3.85.

EXAMPLE 10

2-(2-Thienyl)-2-adamantanemethanamine hydrochloride

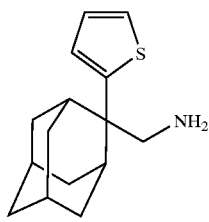

2-(2-Thienyl)-2-adamantanecarbonitrile

This was prepared by the method of example 1 using 2-(2-thienyl)-2-adamantanol in place of 2-(3-ethylphenyl)-2-adamantanol and the product (1.34 g, 78%) isolated as a light brown solid: mp 108–109.5° C.; IR $v_{max}$ (Nujol)/cm$^{-1}$ 2921, 2855, 2227, 1454, 1377, 1240, 1104, 820 and 728; NMR $\delta_H$ (400 MHz, CDCl$_3$) 1.70 (2H, d, J 12.5 Hz), 1.78 (3H, s), 1.97–2.05 (5H, m), 2.46 (2H, d, J 12.5 Hz), 2.64 (2H, s), 7.01–7.06 (2H, m) and 7.33 (1H, d, J 6.5 Hz); Anal. Calcd for $C_{15}H_{17}NS$: C, 74.03; H, 7.04; N, 5.75. Found: C, 74.19; H, 7.09; N, 5.73.

2-(2-Thienyl)-2-adamantanemethanamine hydrochloride

This was prepared by the method of example 1 using 2-(2-thienyl)-2-adamantanecarbonitrile in place of 2-(3-ethylphenyl)-2-adamantanecarbonitrile and the title compound (236 mg, 84%) isolated as a white solid: mp 255–257° C.; IR $v_{max}$ (Nujol)/cm$^{-1}$ 2924, 1592, 1570, 1516, 1457, 1377, 1248, 1100 and 690; NMR $\delta_H$ (400 MHz, CDCl$_3$) 1.65 (5H, s), 1.75–1.99 (7H, m), 3.19 (2H, s), 5.39 (3H, br s), 6.97–6.98 (1H, m) and 7.27–7.29 (2H, m); Anal. Calcd for $C_{15}H_{22}ClNS$: C, 63.47; H, 7.81; N, 4.93. Found: C, 63.64; H, 7.78; N, 4.89.

EXAMPLE 11

2-n-Butyl-2-adamantanemethanamine hydrochloride

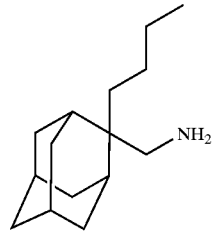

2-n-Butyl-2-adamantanecarbonitrile

This was prepared by the method of example 1 using 2-n-butyl-2-adamantanol in place of 2-(3-ethylphenyl)-2-adamantanol and the product (675 mg, 44%) isolated as a white solid: mp 48–50° C.; IR $v_{max}$ (Nujol)/cm$^{-1}$ 2922, 2228, 1460, 1356 and 1098; NMR $\delta_H$ (400 MHz, CDCl$_3$) 0.95 (3H, t, J 7 Hz), 1.37–1.48 (4H, m), 1.60–1.65 (2H, m), 1.74–1.83 (7H, m), 1.90–1.94 (5H, m) and 2.26 (2H, d, J 13 Hz).

2-n-Butyl-2-adamantanemethanamine hydrochloride

This was prepared by the method of example 1 using 2-n-butyl-2-adamantanecarbonitrile in place of 2-(3-ethylphenyl)-2-adamantanecarbonitrile and the title compound (172 mg, 53%) isolated as a pale solid: mp dec. >250° C.; IR $v_{max}$ (Nujol)/cm$^{-1}$ 3386, 2924, 1984, 1606, 1527, 1490, 1465, 1378, 1099 and 722; NMR $\delta_H$ (400 MHz, CDCl$_3$) 0.90 (3H, t, J 7.5 Hz), 1.07–1.09 (2H, m), 1.29–1.31 (2H, m), 1.51–1.58 (8H, m), 1.64 (2H, s) 1.82 (2H, s), 1.97 (4H, m), 2.96–2.98 (2H, m) and 7.76 (3H, br s); Anal. Calcd for $C_{15}H_{28}NCl$: C, 69.87; H, 10.94; N, 5.43. Found: C, 69.35; H, 10.81; N, 5.39.

II. NMDA Receptor Binding

The NMDA receptor contains several distinct binding domains that can regulate opening of the cationic channel. The phencyclidine (PCP) site of the NMDA receptor can be radiolabeled with [$^3$H]-(+)-5-methyl-10,11-dihydro-5H-dibenzo[a,d]cyclohepten-5,10-imine hydrogen maleate, [$^3$H-MK-801]. The following describes the procedure for determining the affinity of compounds for the PCP site in rat cortical or cerebellar membranes.

Frozen rat cortex or cerebellum, homogenized in 10 volumes of ice-cold 0.32-M. sucrose is centrifuged at 1,000 g for 12 min and the supernatant stored on ice whilst the pellet is resuspended, rehomogenized and recentrifuged twice more. The three final supernatants are pooled and centrifuged at 30,000 g for 40 min at 4° C. to yield $P_2$ pellets. These are resuspended in ice-cold distilled water, and centrifuged at 30,000 g for 50 min at 4° C. Following three further washes in distilled water, the $P_2$ pellets are stored at −20° C. for at least 18 h. On the day of the assay, membrane pellets are thawed at room temperature, resuspended in ice-cold distilled water and centrifuged at 30,000 g for 20 min. The pellets are resuspended in 50-mM tris-HCl (pH:7.4) and recentrifuged twice more before being resuspended in tris-HCl for immediate use in the assay. Binding assays are performed at equilibrium in a total volume of 200 μL, containing [$^3$H]-MK-801 (5-nM final conc.), 10-μM glutamate, 10-μM glycine, 160 μL of membrane preparation and additional drugs where appropriate. Non-specific binding is determined using MK-801 (10-μM). The assay is incubated for 120 min at room temperature. The incubation is terminated by rapid filtration through Whatman GF/B filters (pre-soaked in 0.1% PEI solution). The assay tubes and filters are washed five times with 1 mL of ice-cold assay buffer. The filters are placed in poly-Q mini vials with approximately 5 mL of scintillation fluid. The vials are then shaken and left for at least 8 h before being counted on a liquid scintillation counter. To determine the free ligand concentration 3 aliquots (20 μL) of the [$^3$H]-MK-801 working solution are also counted. Concentration response data for drugs is analysed using a 4 parameter equation fitted by non-linear regression. This yields the half maximally effective drug concentration ($IC_{50}$) and Hill coefficient. The data obtained from these assays are presented in Table 1. The data clearly demonstrate that the compounds of the invention are active as NMDA antagonists and have favourable ratios of cortical to cerebellar binding affinity indicating that the compounds will be well-tolerated in vivo.

TABLE 1

Binding Affinities at Cortical and Cerebellar NMDA Receptors

| Compound | $IC_{50}(\mu M)$ Cortex | $IC_{50}(\mu M)$ Cerebellum | Ratio |
| --- | --- | --- | --- |
| Example 1 | 27 | 14 | 1.9 |
| Example 2 | 13 | 6 | 2.2 |
| Example 3 | 87 | 21 | 4.1 |
| Example 4 | 124 | 33 | 3.8 |
| Example 6 | 53 | 48 | 1.1 |
| Example 7 | 103 | 68 | 1.5 |
| Example 8 | 51 | 24 | 2.1 |
| Example 9 | 189 | 110 | 1.7 |
| Example 10 | 33 | 20 | 1.7 |

What is claimed is:

1. A method of treating a condition treatable by antagonism of the N-methyl-D-aspartate receptor, comprising administering to a subject suffering from said condition a pharmaceutically effective amount of a compound of the formula (1):

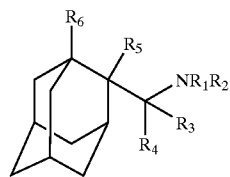

(1)

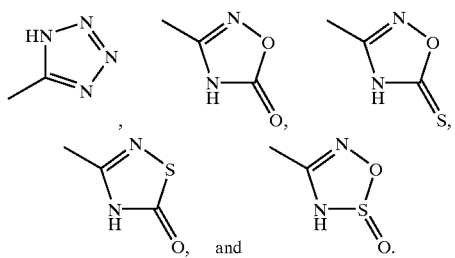

wherein $R_1$, $R_2$, $R_3$, $R_4$, $R_5$ and $R_6$ are independently selected from hydrogen, alkyl and aryl, or a pharmaceutically acceptable salt thereof, with the proviso that wherein $R_1$ to $R_4$ and $R_6$ are hydrogen, $R_5$ is not selected from $CH_2CH_2NHSO_2CH_3$, $CH_2CH_2NHSO_2CF_3$ and methyl substituted by $SO_2NH_2$, $SO_3H$, $PO_3H_2$, CONHOH or a heterocyclic group selected from 2. A method according to claim 1, wherein one or more of $R_1$, $R_2$, $R_3$, $R_4$ and $R_6$ are hydrogen.

3. A method according to claim 1, wherein one or both of $R_1$ and $R_2$ are hydrogen.

4. A method according to claim 1, wherein one or both of $R_3$ and $R_4$ are hydrogen.

5. A method according to claim 1, wherein $R_5$ is alkyl.

6. A method according to claim 1, wherein $R_5$ is an acyclic hydrocarbyl radical.

7. A method according to claim 1, wherein $R_5$ is aryl.

8. A method according to claim 1, wherein $R_5$ is substituted or unsubstituted phenyl.

9. A method according to claim 8, wherein $R_5$ is phenyl substituted by a substituent selected from the group consisting of methyl, ethyl, fluorine, chlorine, methoxy and trifluoromethyl.

10. A method according to claim 9, wherein said phenyl is meta-substituted.

11. A method according to claim 1, wherein $R_5$ is 3-methylphenyl, 4-methylphenyl or 3-ethylphenyl.

12. A method according to claim 1, wherein said compound is selected from the group consisting of:

2-(3-ethylphenyl)-2-adamantanemethanamine;

2-(3-methylphenyl)-2-adamantanemethanamine;

2-phenyl-2-adamantanemethanamine; and 2-(4-methylphenyl)-2-adamantanemethanamine.

13. The method of claim 1 wherein said condition treatable by antagonism of the N-methyl-D-aspartate receptor is selected from the group consisting of ischaemic stroke, haemorrhagic stroke, subarachnoid haemorrhage, subdural haematoma, coronary artery bypass surgery, neurosurgery, traumatic brain injury, traumatic spinal injury, Alzheimer's disease, Parkinson's disease, Huntington's disease, Pick's disease, Lewy body disease, senile dementia, spongiform encephalopathies, prion-protein induced neurotoxicity, perinatal asphyxia, demyelinating disease, multiinfarct dementia, vascular dementia, dementia pugilans, drug dependence, alcohol withdrawal, opiate withdrawal, motor neurone disease, multiple sclerosis, acute pain, chronic pain, diabetic neuropathy, epilepsy, AIDS dementia, multiple system atrophy, progressive supra-nuclear palsy, Friedrich's ataxia, autism, fragile X syndrome, tuberous sclerosis, attention deficit disorder, olivio-ponto-cerebellar atrophy, cerebral palsy, drug-induced optic neuritis, peripheral neuropathy, myelopathy, ischaemic retinopathy, glaucoma, cardiac arrest, meningitis, encephalitis, depression, bi-polar disorder, schizophrenia, psychosis, behaviour disorders, impulse control disorders, pre-eclampsia, neuroleptic malignant syndrome, chronic fatigue syndrome, anorexia nervosa, anxiety disorders, generalised anxiety disorder, panic disorder, phobias, fresh water drowning and decompression.

14. The method of claim 1 wherein said condition treatable by antagonism of the N-methyl-D-aspartate receptor is selected from the group consisting of ischaemic stroke, haemorrhagic stroke, subarrachnoid haemorrhage, subdural haematoma, coronary artery bypass surgery, neurosurgery, traumatic brain injury, traumatic spinal injury, Alzheimer's disease, Parkinson's disease, Huntington's disease, senile dementia, peri-natal asphyxia, multiinfarct dementia, drug dependence, alcohol withdrawal, opiate withdrawal, motor neurone disease, multiple sclerosis, acute pain, chronic pain, epilepsy, progressive supranuclear palsy, autism, cerebral palsy, drug-induced optic neuritis, peripheral neuropathy, myelopathy, ischaemic retinopathy, glaucoma, cardiac arrest, depression, schizophrenia, anxiety disorders and generalized anxiety disorder.

15. The method of claim 1 wherein said condition treatable by antagonism of the N-methyl-D-aspartate receptor is selected from the group consisting of neuropathic pain, cancer pain, trigeminal neuralgia, migraine, primary and secondary hyperalgesia, inflammatory pain, nociceptive pain, tabes dorsalis, phantom limb pain, spinal cord injury pain, central pain, post-herpetic pain and HIV pain.

16. A pharmaceutical composition comprising a compound of the formula (1):

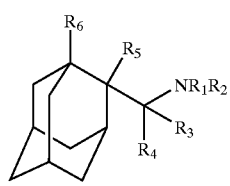

(1)

wherein $R_1$, $R_2$, $R_3$, $R_4$, $R_5$ and $R_6$ are independently selected from hydrogen, alkyl and aryl, or a pharmaceutically acceptable salt thereof, with the proviso that wherein $R_1$ to $R_4$ and $R_6$ are hydrogen, $R_5$ is not selected from $CH_2CH_2NHSO_2CH_3$, $CH_2CH_2NHSO_2CF_3$ and methyl substituted by $SO_2NH_2$, $SO_3H$, $PO_3H_2$, $CONHOH$ or a heterocyclic group selected from

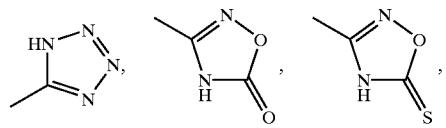

-continued

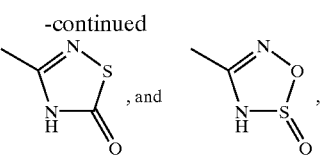

, and in association with a pharmaceutically acceptable diluent or carrier.

17. A pharmaceutical composition according to claim 16, other than a compound in which $R_3$, $R_4$, $R_5$ and $R_6$ are hydrogen and $R_1$ and $R_2$ are independently selected from alkyl and other than a compound in which $R_1$, $R_2$, $R_5$ and $R_6$ are hydrogen and $R_3$ and $R_4$ are independently selected from alkyl.

18. A pharmaceutical composition according to claim 16, wherein
(i) $R_3$, $R_4$, $R_5$ and $R_6$ are independently selected from hydrogen, alkyl and aryl and $R_1$ and $R_2$ are independently selected from hydrogen and aryl; or
(ii) $R_3$, $R_4$, $R_5$ and $R_6$ are independently selected from alkyl and aryl and $R_1$ and $R_2$ are independently selected from alkyl; or
(iii) $R_1$, $R_2$, $R_5$ and $R_6$ are independently selected from hydrogen, alkyl and aryl and $R_3$ and $R_4$ are independently selected from hydrogen and aryl; or
(iv) $R_1$, $R_2$, $R_5$ and $R_6$ are independently selected from alkyl and aryl and $R_3$ and $R_4$ are independently selected from alkyl.

19. A pharmaceutical composition according to claim 16 wherein $R_5$ is selected from alkyl and aryl, and pharmaceutically acceptable salts thereof.

20. A compound of the formula (1):

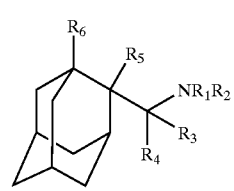

(1)

wherein $R_1$, $R_2$, $R_3$, $R_4$, $R_5$ and $R_6$ are independently selected from hydrogen, alkyl and aryl, with the proviso that wherein $R_1$ to $R_4$ and $R_6$ are hydrogen, $R_5$ is not selected from $CH_2CH_2NHSO_2CH_3$, $CH_2CH_2NHSO_2CF_3$ and methyl substituted by $SO_2NH_2$, $SO_3H$, $PO_3H_2$, $CONHOH$ or a heterocyclic group selected from

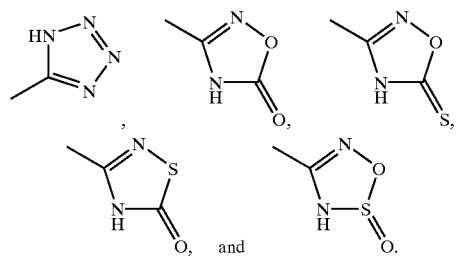

21. A pharmaceutical composition comprising a compound according to claim 20, in combination with a pharmaceutically acceptable excipient.

22. A method of treating a condition treatable by antagonism of the N-methyl-D-aspartate receptor, comprising administering to a patient suffering from such condition a pharmaceutically effective amount of a compound of formula (1):

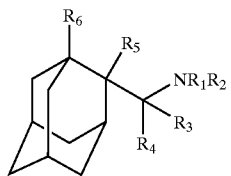
(1)

wherein $R_1$, $R_2$, $R_3$, $R_4$, $R_5$ and $R_6$ are independently selected from hydrogen, alkyl and aryl, wherein each alkyl is independently a branched or unbranched, cyclic or acyclic, saturated or unsaturated, optionally substituted hydrocarbyl radical, wherein each aryl is independently an optionally substituted carbocyclic aromatic group, or an optionally substituted heteroaromatic group, or an optionally substituted heteroaromatic group, wherein said optional substituent is selected from alkyl, aryl, arylalkyl, haloalkyl, hydroxy, hydroxyalkyl, aryl(hydroxy)alkyl, alkoxy, aryloxy, alkoxyalkyl, aryloxyalkyl, carboxaldehyde, alkylcarbonyl, alkylcarbonylalkyl, arylcarbonyl, arylalkylcarbonyl, arylcarbonylalkyl, carboxy, carboxyalkyl, alkoxycarbonyl, alkoxycarbonylalkyl, alkylcarbonyloxy, alkylcarbonyloxyalkyl, aminocarbonyl, mono- or di-alkylaminocarbonyl, aminocarbonylalkyl, mono- or di-alkylaminocarbonyl, arylaminocarbonyl, alkoxycarbonylamino, aryloxycarbonylamino, aminocarbonyloxy, mono- or di-alkylaminocarbonyloxy, arylaminocarbonyloxy, mono- or di-alkylaminocarbonylamino, arylaminocarbonylamino, amino, mono- or di-alkylamino, aminoalkyl, mono- or di-alkylaminoalkyl, azides, cyano, cyanoalkyl, nitro, alkylthio, alkylsulfinyl, alkylsulfonyl, alkylthioalkyl, alkylsulfmylalkyl, alkylsulfonylalkyl, arylthio, arylsulfinyl, arylsulfonyl, arylthioaylkyl, arylsulfinylalkyl, arylsulfonylalkyl, thienyl, furanyl, pyrrolyl, imidazolyl, pyrazolyl, thiazotyl, isothiazolyl, oxazolyl, oxadiazolyl, thiadiazolyl, aziridinyl, azetidinyl, pyrrolidinyl, pyrrolinyl, imidazolidinyl, imidazolidinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, benzothienyl, benzofuranyl, isobenzofuranyl, indolyl, oxyindolyl, isoindolyl, indazolyl, indolinyl, 7-azaindolyl, indolizinyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl, or a pharmaceutically acceptable salt thereof, with the proviso that wherein $R_1$ to $R_4$ and $R_6$ are hydrogen, $R_5$ is not selected from $CH_2CH_2NHSO_3CH_3$, $CH_2CH_2NHSO_2CF3$ and methyl substituted by $SO_2NH_2$, $SO_3H$, $PO_3H_2$, $CONHOH$ or a heterocyclic group selected from

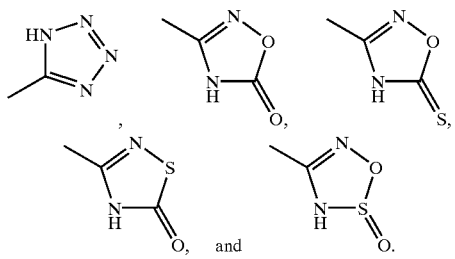

23. A method according to claim 22 wherein said alkyl is independently a branched or unbranched, $C_3$ to $C_{12}$ cyclic or $C_3$ to $C_{10}$ acyclic, saturated or unsaturated, optionally substituted hydrocarbyl radical, and each aryl is independently an optionally substituted carbocyclic aromatic group selected from the group consisting of phenyl and naphthyl, or an optionally substituted heteroaromatic group containing at least one heteroatom and selected from the group consisting of pyridyl, pyrrolyl, furanyl, thienyl, thiazolyl, isothiazolyl, oxazolyl, isoxazolyl, oxadiazolyl, thiadiazolyl pyrazolyl, imidazolyl, triazolyl, pyrimidinyl pyridazinyl, pyrazinyl, triazinyl, indolyl, indazolyl, quinolyl, quinazolyl, benzimidazolyl, benzothiazolyl, benzisoxazolyl and benzisothiazolyl, and wherein when said alkyl and/or said aryl groups are substituted, 1 to 3 substituents are present.

24. A pharmaceutical composition comprising a compound of formula (1):

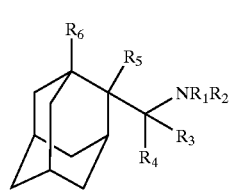
(1)

wherein $R_1$, $R_2$, $R_3$, $R_4$, $R_5$ and $R_6$ are independently selected from hydrogen, alkyl and aryl, wherein each alkyl is independently a branched or unbranched, cyclic or acyclic, saturated or unsaturated, optionally substituted hydrocarbyl radical, wherein each aryl is independently an optionally substituted carbocyclic aromatic group, or an optionally substituted heteroaromatic group, wherein said optional substituent is selected from alkyl, aryl, arylalkyl, haloalkyl, hydroxy, hydroxyalkyl, aryl(hydroxy)alkyl, alkoxy, aryloxy, alkoxyalkyl, aryloxyalkyl, carboxaldehyde, alkylcarbonyl, alkylcarbonylalkyl, arylcarbonyl, arylalkylcarbonyl, arylcarbonylalkyl, carboxy, carboxyalkyl, alkoxycarbonyl, alkoxycarbonylalkyl, alkylcarbonyloxy, alkylcarbonyloxyalkyl, aminocarbonyl, mono- or di-alkylaminocarbonyl, aminocarbonylalkyl, mono- or di-alkylaminocarbonyl, arylaminocarbonyl, alkoxycarbonylamino, aryloxycarbonylamino, aminocarbonyloxy, mono- or di-alkylaminocarbonyloxy, arylaminocarbonyloxy, mono- or di-alkylaminocarbonylamino, arylaminocarbonylamino, amino, mono- or di-alkylamino, aminoalkyl, mono- or di-alkylaminoalkyl, azides, cyano, cyanoalkyl, nitro, alkylthio, alkylsulfinyl, alkylsulfonyl, alkylthioalkyl, alkylsulfinylalkyl, alkylsulfonylalkyl, arylthio, arylsulfinyl, arylsulfonyl, arylthioaylkyl, arylsulfinylalkyl, arylsulfonylalkyl, thienyl, furanyl, pyrrolyl, imidazolyl, pyrazolyl, thiazotyl, isothiazolyl, oxazolyl, oxadiazolyl, thiadiazolyl, aziridinyl, azetidinyl, pyrrolidinyl, pyrrolinyl, imidazolidinyl, imidazolidinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, benzothienyl, benzofuranyl, isobenzofuranyl, indolyl, oxyindolyl, isoindolyl, indazolyl, indolinyl, 7-azaindolyl, indolizinyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl, or a pharmaceutically acceptable salt thereof, with the proviso that wherein $R_1$ to $R_4$ and $R_6$ are hydrogen, $R_5$ is not selected from $CH_2CH_2NHSO_3CH_3$, $CH_2CH_2NHSO_2CF_3$ and methyl substituted by $SO_2NH_2$, $SO_3H$, $PO_3H_2$, CONHOH or a heterocyclic group selected from

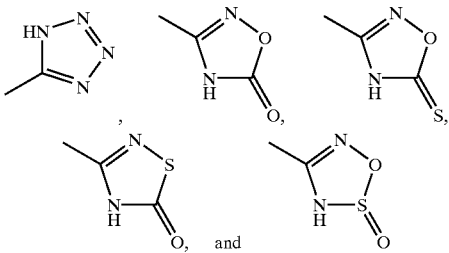

other than a compounds in which $R_3$, $R_4$, $R_5$ and $R_6$ are hydrogen and one of $R_1$ and $R_2$ is hydrogen, methyl or benzyl and one of $R_1$ and $R_2$ is a substituted methyl, ethyl or propyl group, and other than a compound in which $R_1$, $R_2$, $R_5$ and $R_6$ are hydrogen and $R_3$ and $R_4$ are selected from methyl and aminomethyl, in association with a pharmaceutically acceptable diluent or carrier.

25. A pharmaceutical composition according to claim 24 wherein said alkyl is independently a branched or unbranched, $C_3$ to $C_{12}$ cyclic or $C_3$ to $C_{10}$ acyclic, saturated or unsaturated, optionally substituted hydrocarbyl radical, and each aryl is independently an optionally substituted carbocyclic aromatic group selected from the group consisting of phenyl and naphthyl, or an optionally substituted heteroaromatic group containing at least one heteroatom and selected from the group consisting of pyridyl, pyrrolyl, furanyl, thienyl, thiazolyl, isothiazolyl, oxazolyl, isoxazolyl, oxadiazolyl, thiadiazolyl pyrazolyl, imidazolyl, triazolyl, pyrimidinyl pyridazinyl, pyrazinyl, triazinyl, indolyl, indazolyl, quinolyl, quinazolyl, benzimidazolyl, benzothiazolyl, benzisoxazolyl and benzisothiazolyl, and wherein when said alkyl and/or said aryl groups are substituted, 1 to 3 substituents are present.

26. A compound of formula (1):

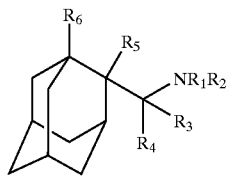

(1)

wherein $R_1$, $R_2$, $R_3$, $R_4$ and $R_6$ are independently selected from hydrogen, alkyl and aryl, and $R_5$ is selected from alkyl and aryl, wherein each alkyl is independently a branched or unbranched, cyclic or acyclic, saturated or unsaturated, optionally substituted hydrocarbyl radical, wherein each is independently an optionally substituted carbocyclic aromatic group, or an optionally substituted heteroaromatic group, wherein said optional substituent is selected from alkyl, aryl, arylalkyl, haloalkyl, hydroxy, hydroxyalkyl, aryl (hydroxy)alkyl, alkoxy, aryloxy, alkoxyalkyl, aryloxyalkyl, carboxaldehyde, alkylcarbonyl, alkylcarbonylalkyl, arylcarbonyl, arylalkylcarbonyl, arylcarbonylalkyl, carboxy, carboxyalkyl, alkoxycarbonyl, alkoxycarbonylalkyl, alkylcarbonyloxy, alkylcarbonyloxyalkyl, aminocarbonyl, mono- or di-alkylaminocarbonyl, aminocarbonylalkyl, mono- or di-alkylaminocarbonyl, arylaminocarbonyl, alkoxycarbonylamino, aryloxycarbonylamino, aminocarbonyloxy, mono- or di-alkylaminocarbonyloxy, arylaminocarbonyloxy, mono- or di-alkylaminocarbonylamino, arylaminocarbonylamino, amino, mono- or di-alkylamino, aminoalkyl, mono- or di-alkylaminoalkyl, azides, cyano, cyanoalkyl, nitro, alkylthio, alkylsulfinyl, alkylsulfonyl, alkylthioalkyl, alkylsulfinylalkyl, alkylsulfonylalkyl, arylthio, arylsulfinyl, arylsulfonyl, arylthioaylkyl, arylsulfinylalkyl, arylsulfonylalkyl, thienyl, furanyl, pyrrolyl, imidazolyl, pyrazolyl, thiazotyl, isothiazolyl, oxazolyl, oxadiazolyl, thiadiazolyl, aziridinyl, azetidinyl, pyrrolidinyl, pyrrolinyl, imidazolidinyl, imidazolidinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, benzothienyl, benzofuranyl, isobenzofuranyl, indolyl, oxyindolyl, isoindolyl, indazolyl, indolinyl, 7-azaindolyl, indolizinyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl, or a pharmaceutically acceptable salt thereof, with the proviso that wherein $R_1$ to $R_4$ and $R_6$ are hydrogen, $R_5$ is not selected from $CH_2CH_2NHSO_2CH_3$, $CH_2CH_2NHSO_2CF_3$ and methyl substituted by $SO_2NH_2$, $SO_3H$, $PO_3H_2$, CONHOH or a heterocyclic group selected from

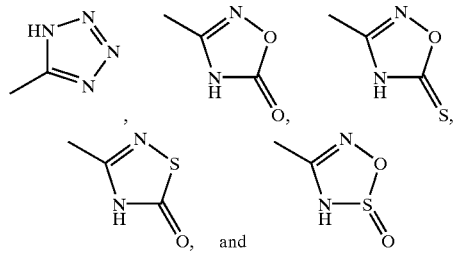

other than a compound in which $R_1$ and $R_2$ are methyl, $R_3$, $R_4$ and $R_6$ are hydrogen and $R_5$ is hydroxymethyl.

27. A compound according to claim 26 wherein said alkyl is independently a branched or unbranched, $C_3$ to $C_{12}$ cyclic or $C_3$ to $C_{10}$ acyclic, saturated or unsaturated, optionally substituted hydrocarbyl radical, and each aryl is independently an optionally substituted carbocyclic aromatic group selected from the group consisting of phenyl and naphthyl, or an optionally substituted heteroaromatic group containing at least one heteroatom and selected from the group consisting of pyridyl, pyrrolyl, furanyl, thienyl, thiazolyl, isothiazolyl, oxazolyl, isoxazolyl, oxadiazolyl, thiadiazolyl pyrazolyl, imidazolyl, triazolyl, pyrimidinyl pyridazinyl, pyrazinyl, triazinyl, indolyl, indazolyl, quinolyl, quinazolyl, benzimidazolyl, benzothiazolyl, benzisoxazolyl and benzisothiazolyl, and wherein when said alkyl and/or said aryl groups are substituted, 1 to 3 substituents are present.

* * * * *